United States Patent
Cotteret et al.

[11] Patent Number: 5,993,791
[45] Date of Patent: Nov. 30, 1999

[54] OXIDATION DYE COMPOSITION FOR KERATINOUS FIBRES COMPRISING A PARA-AMINOPHENOL, A META-AMINOPHENOL AND A 2-SUBSTITUTED PARA-AMINOPHENOL

[75] Inventors: Jean Cotteret, Verneuil-sur-Seine; Marie Pascale Audousset, Levallois-Perret; Alain Lagrange, Coupvray; Jean Jacques Vandenbosche, Sevran, all of France

[73] Assignee: L'Oreal, Paris, France

[21] Appl. No.: 08/810,799

[22] Filed: Mar. 6, 1997

Related U.S. Application Data

[63] Continuation of application No. 08/273,749, Jul. 13, 1994, abandoned.

[30] Foreign Application Priority Data

Jul. 13, 1993 [FR] France .................................. 93 08617

[51] Int. Cl.$^6$ ...................................................... A61K 7/13
[52] U.S. Cl. .............................. 424/70.1; 424/47; 8/407; 8/408; 8/412; 8/421
[58] Field of Search ......................... 424/70.1, 47; 8/407, 8/408, 412, 421

[56] References Cited

U.S. PATENT DOCUMENTS 4,997,451  3/1991  Clausen .
5,053,052  10/1991  Junino .
5,202,487  4/1993  Junino .

FOREIGN PATENT DOCUMENTS 0 359 618  3/1990  European Pat. Off. .
0 395 837  11/1990  European Pat. Off. .

*Primary Examiner*—Jyothsna Venkat
*Attorney, Agent, or Firm*—Nixon & Vanderhye, P.C.

[57] ABSTRACT

The invention relates to a dyeing composition for keratinous fibers and in particular for human keratinous fibers such as hair, comprising, in a suitable medium for dyeing, at least one oxidation dye precursor chosen from 3-methyl-para-aminophenol, 2-methyl-para-aminophenol and 2-hydroxymethyl-para-aminophenol, and their addition salts with an acid; at least one coupling agent chosen from the 2-methyl-5-aminophenols of formula (I):

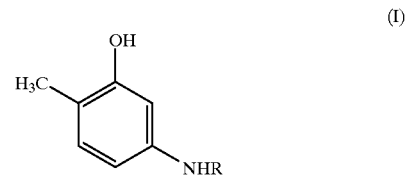

in which R denotes hydrogen, methyl or ethyl or a β-hydroxyethyl or γ-hydroxypropyl group, and their addition salts with an acid; and as oxidation dye precursor, a para-aminophenol which is 2-substituted by a substituent which is different from methyl or hydroxymethyl, or one of its addition salts with an acid.

26 Claims, No Drawings

OXIDATION DYE COMPOSITION FOR KERATINOUS FIBRES COMPRISING A PARA-AMINOPHENOL, A META-AMINOPHENOL AND A 2-SUBSTITUTED PARA-AMINOPHENOL

This is a continuation of application Ser. No. 08/273,749, filed Jul. 13,1994 now abandoned.

The present invention relates to a dyeing composition for keratinous fibers, and in particular for human keratinous fibers, comprising, in combination, at least one para-aminophenol, at least one 2-substituted 5-aminophenol and at least one 2-substituted para-amino-phenol, and to the dyeing process using such a composition and implementing its development by an oxidizing agent.

It is known to dye keratinous fibers and in particular human hair, with dyeing compositions containing oxidation dye precursors, in particular ortho- or para-phenylenediamines, ortho- or para-aminophenols, generally known as "oxidation bases" and coupling agents, also known as dyeing modifiers, more particularly aromatic meta-phenylene diamines, meta-aminophenols and meta-diphenols, which allow the "foundation" colourations obtained by the condensation products of the oxidation bases to be modified and to be enriched with glints.

In the field of oxidation dyeing of hair, oxidation dye precursors and coupling agents are sought which allow a colouration having a satisfactory resistance to light, to washing, to bad weather, to perspiration and to the various treatments to which hair may be subjected to be imparted to the hair, and to obtain a wide range of colour shades.

3-Methyl-para-aminophenol, as well as its use in dyeing compositions for keratinous fibers, in combination with 2-methyl-5-aminophenol as coupling agent and para-phenylenediamine or 2,5-diaminotoluene, are known and described in U.S. Pat. No. 4,883,656.

However, such a combination does not provide, after application to keratinous fibers, a sufficiently resistant colouration.

The Applicant has just discovered, and this forms the subject of the invention, that the use of 3-methyl-para-aminophenol, 2-methyl-para-aminophenol and/or 2-hydroxymethyl-para-aminophenol as oxidation dye precursors, in combination with, as coupling agent, at least one 5-aminophenol which is substituted in the 2-position, chosen from the 2-methyl-5-aminophenols of formula (I) defined below and, as oxidation dye precursor, at least one other para-aminophenol which is substituted in the 2-position by a substituent which is different from methyl and hydroxymethyl, makes it possible to obtain, in the presence of an oxidizing agent, in an acidic or alkaline medium, after application to keratinous fibers and in particular human hair, colourations with warm and coppery shades and which have a good resistance to light, to washing, to bad weather, to perspiration and to the various treatments to which hair may be subjected.

The subject of the present invention is thus a composition for dyeing keratinous fibers, in particular human keratinous fibers such as hair, comprising, in a suitable medium for dyeing:
  at least: one oxidation dye precursor chosen from 3-methyl-para-aminophenol, 2-methyl-para-aminophenol and 2-hydroxymethyl-para-aminophenol, and their addition salts with an acid;
  at least one coupling agent chosen from the 2- methyl-5-aminophenols of formula (I) below:

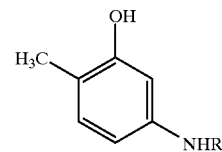

(I)

in which R denotes a hydrogen atom, a methyl or ethyl radical or a β-hydroxyethyl or γ-hydroxypropyl group, and their addition salts with an acid; and
  as oxidation dye precursor, at least one 2-substituted para-aminophenol of formula (II) below, or one of its addition salts with an acid.

The subject of the invention is also a dyeing agent containing several components, the first component of which contains oxidation dye precursors and the coupling agent defined above and the second component an oxidizing agent.

Another subject of the invention relates to the ready-to-use composition, containing the various agents used for dyeing keratinous fibers defined above and an oxidizing agent, in an alkaline or acidic medium.

The invention also concerns a process for dyeing keratinous fibers, and in particular human keratinous fibers such as hair, consisting in applying to these fibers:
  at least one oxidation dye precurser chosen from 3-methyl-para-aminophenol, 2-methyl-para-aminophenol and 2-hydroxymethyl-para-aminophenol and their addition salts with an acid;
  at least one coupling agent chosen from the 2-methyl-5-aminophenols of formula (I) defined above, and their addition salts with an acid;
  as oxidation dye precursor, at least one 2-substituted para-aminophenol of formula (II) below, or one of its addition salts with an acid;
  the colour being developed at acidic or basic pH, using an oxidizing agent.

According to the invention and among the above-mentioned three precursors of para-aminophenol type, 3-methyl-p-aminophenol is preferred.

Among the coupling agents mentioned above, it is preferred for 2-methyl-5-aminophenol, 2-methyl-5-N-(β-hydroxyethyl) aminophenol, 2-methyl-5-methylaminophenol and 2-methyl-5-ethylaminophenol to be used according to the invention.

The 2-substituted para-aminophenols used according to the invention correspond to the formula (II) below:

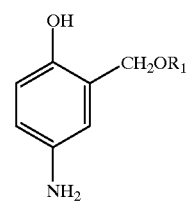

(II)

in which $R_1$ represents a $C_1$–$C_6$ alkyl, $C_1$–$C_6$ hydroxyalkyl, $C_2$–$C_6$, polyhydroxyalkyl, $C_1$–$C_6$ haloalkyl or $C_2$–$C_4$ amino-alkyl radical or a $C_2$–$C_4$ aminoalkyl radical in which the amine may be mono- or disubstituted with a $C_1$–$C_4$ alkyl group or substituted with a $C_3$–$C_4$ dihydroxyalkyl group.

These compounds may be used in free or salified form.

Among the compounds of formula (II) above, there may in particular be mentioned:

2-methoxymethyl-para-aminophenol,
2-ethoxymethyl-para-aminophenol,
2-n-propyloxymethyl-para-aminophenol,
2-isopropyloxymethyl-para-aminophenol,
2-(β-hydroxyethoxy)methyl-para-aminophenol,
2-[(2', 2', 2'-trifluoroethoxy)methyl]para-aminophenol,
and their salts.

2-Methoxymethyl-para-aminophenol or one of its addition salts with an acid is more particularly preferred.

According to the process in accordance with the invention, at least one composition (A) is applied to human keratinous fibers, containing, in a suitable medium for dyeing:

at least one oxidation dye precursor chosen from 3-methyl-para-aminophenol, 2-methyl-para-aminophenol, 2-hydroxymethyl-para-aminophenol, and their salts;

at least one coupling agent chosen from the 2-methyl-5-aminophenols of formula (I) defined above, and their salts;

at least one 2-substituted para-aminophenol of formula (II) defined above or one of its salts;

the colour being developed in an acidic or alkaline medium, using an oxidizing agent which is added just at the moment of use to the composition (A) or which is present in a composition (B) which is applied simultaneously or sequentially in a separate manner.

The subject of the invention is also dyeing devices or "kits", containing several compartments, allowing the process indicated above to be implemented.

Such a dyeing kit contains at least two compartments, the first of which contains the composition (A) as defined above and the second contains the composition (B) comprising an oxidizing agent in a suitable medium for dyeing.

Other subjects of the invention will become apparent on reading the description and the examples which follow.

The acid salts used according to the invention are preferably chosen from hydrochlorides, sulphates, hydrobromides and tartrates.

3-Methyl-para-aminophenol, 2-methyl-para-aminophenol and 2-hydroxymethyl-para-aminophenol or their salts are present at a total concentration of 0.01% to 4% by weight relative to the total weight of the dyeing composition, and preferably from 0.1 to 2% by weight.

The 2-methyl-5-aminophenols of formula (I) and their salts represent in total from 0.05% to 5% by weight relative to the total weight of the dyeing composition, and preferably from 0.1 to 3.5% by weight.

The 2-substituted para-aminophenols of formula (II) represent from 0.05 to 4% by weight relative to the total weight of the dyeing composition, and preferably from 0.2 to 2% by weight.

The set of oxidation dye precursors and coupling agents according to the invention represents from 0.15 to 10% by weight, and preferably from 0.4 to 7% by weight, relative to the total weight of the composition.

The oxidizing agent is preferably chosen from hydrogen peroxide, urea peroxide, alkali metal bromates and persalts such as perborates and persulphates. Hydrogen peroxide is particularly preferred.

The composition (A), which contains the combination of dyes as described above, may have a pH between 3 and 10.5, which may be adjusted to the chosen value using basifying agents commonly used in the dyeing of keratinous fibers, such as aqueous ammonia, alkali metal carbonates, alkanolamines, for example mono-, di- and triethanolamines and their derivatives, sodium or potassium hydroxides, the compounds of formula:

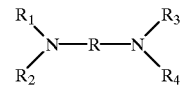

in which:

R is a propylene residue which is optionally substituted with a hydroxyl group or with a $C_1$–$C_4$ alkyl radical;

$R_1$, $R_2$, $R_3$ and $R_4$ simultaneously or independently of each other, represent a hydrogen atom, a $C_1$–$C_4$ alkyl radical or a $C_1$–$C_4$ hydroxyalkyl radical; or standard acidifying agents, such as inorganic or organic acids, for example hydrochloric, tartaric, citric and phosphoric acids.

The pH of the composition (B) containing the oxidizing agent as defined above is such that after mixing with the composition (A), the pH of the composition applied to human keratinous fibers preferably varies between 3 and 11. It is adjusted to the desired value using acidifying or possibly basifying agents which are well known in the state of the art, as described above.

The oxidizing composition (B) preferably consists of hydrogen peroxide solution.

According to a preferred embodiment of the dyeing process of the invention, the dyeing composition (A) described above is mixed at the moment of use with an oxidizing solution in a sufficient amount to develop a colouration. The mixture obtained is subsequently applied to human keratinous fibers and is left to stand for 5 to 40 minutes, preferably 15 to 30 minutes, after which the fibers are rinsed, washed with shampoo, rinsed again and dried.

According to the invention, the dyeing compositions may contain, in addition to the dyes defined above, other coupling agents and/or direct dyes, in particular for the purpose of tinting or enriching with glints the colourations provided by the oxidation dye precursors.

These coupling agents are well known per se and are chosen from benzene compounds bearing at least 2 hydroxyl and/or optionally modified amino substitutions in a meta position with respect to each other and which are different from the 2-methyl-5-aminophenols of formula (I), and their salts; α-naphthol; indole derivatives; coupling agents possessing an active methylene group, such as β-keto compounds; pyrazolones; as well as their salts.

The direct dyes are preferably azo or anthraquinone dyes or nitro derivatives of the benzene series.

The dyeing compositions in accordance with the invention also contain, in their preferred embodiment, anionic, cationic, nonionic or amphoteric surface-active agents or their mixtures. Among these surface-active agents there may be mentioned alkylbenzene sulphonates, alkylnaphthalene sulphonates, sulphates, ether sulphates and fatty alcohol sulphonates, alkylpolyglycosides, quaternary ammonium salts such as trimethylcetylammonium bromide, cetylpyridinium bromide, optionally oxyethylenated fatty acid ethanolamides, polyoxyethyenated acids, alcohols and amines, polyglycerolated fatty alcohols, and polyoxyethylenated or polyglycerolated alkylphenols, as well as polyoxyethylenated alkyl sulphates.

These surface-active agents are present in the compositions in accordance with the invention in proportions between 0.5 and 55% by weight and preferably between 2 and 50% by weight relative to the total weight of the composition.

These compositions may also contain organic solvents for dissolving the compounds which would not be sufficiently soluble in water. Among these solvents, there may be mentioned, by way of example, $C_1$–$C_4$ lower alkanols such as ethanol and isopropanol; glycerol, glycols or glycol ethers such as 2-butoxyethanol, propylene glycol, the monoethyl ether and the monomethyl ether of diethylene glycol, and aromatic alcohols such as benzyl alcohol or phenoxyethanol, analogous products and their mixtures.

The solvents are preferably present in proportions between 1 and 40% by weight and in particular between 5 and 30% by weight relative to the total weight of the composition.

The thickening agents which may be added to the compositions in accordance with the invention may be chosen from sodium alginate, gum arabic, optionally crosslinked acrylic acid polymers, cellulose derivatives and heterobiopolysaccharides such as xanthan gum, and inorganic thickening agents such as bentonite may also be used.

These thickening agents are preferably present in proportions between 0.1 and 5% and in particular between 0.2 and 3% by weight relative to the total weight of the composition.

The antioxidants which may be present in the compositions are chosen in particular from sodium sulphite, thioglycolic acid, thiolactic acid, sodium bisulphite, dehydroascorbic acid, hydroquinone, 2-methyl-hydroquinone, tert-butylhydroquinone and homogentisic acid.

These antioxidants are present in the composition in proportions between 0.05 and 1.5% by weight relative to the total weight of the composition.

These compositions may also contain other cosmetically acceptable adjuvants, such as for example penetration agents, sequestering agents, perfumes, buffers, dispersing agents, treatment agents, conditioning agents, film-forming agents, preservatives and opacifying agents.

The composition applied to hair may be provided in various forms, such as in liquid, cream or gel form or any other form which is suitable for dyeing keratinous fibers and in particular human hair. These compositions may be packaged under pressure in aerosol cans in the presence of a propellent and may form foams.

The examples which follow are intended to illustrate the invention without, however, presenting a limiting nature.

Dyeing at Basic pH

EXAMPLES 1 to 3

The following dyeing composition is prepared:

| | |
|---|---|
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oxyethylenated oleic amine containing 2 mol of ethylene oxide, sold under the name ETHOMEEN O12 by the company AKZO | 7.0 g |
| Diethylaminopropyl laurylaminosuccinamate, sodium salt containing 55% of AM | 3.0 g AM |
| Oleyl alcohol | 5.0 g |
| Oleic acid diethanolamide | 12.0 g |
| Propylene glycol 3.5 g | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% of AM | 0.46 g AM |
| Ammonium acetate | 0.8 g |
| Antioxidant, sequestering agent | qs |
| Perfume, preservative | qs |
| Aqueous ammonia containing 20% of $NH_3$ | 10.0 g |
| Colouring agents | x g |
| Demineralized water | qs 100 g |

At the time of use, this composition is mixed, weight for weight, with hydrogen peroxide titrating at 20 volumes (6% by weight), of pH 3.

A mixture is obtained of pH indicated in the table below.

This mixture is applied to grey hair containing 90% natural or permanent-waved white hair for 30 minutes. After rinsing, washing with shampoo, rinsing and drying, the hair is dyed in the shades indicated in the table below.

TABLE

| Example | 1 | 2 | 3 |
|---|---|---|---|
| 3-methyl-para-aminophenol | 1 g | | 1 g |
| 2-methyl-para-aminophenol | | 0.5 g | |
| 2-hydroxymethyl-para-aminophenol | | 0.5 g | |
| 2-methyl-5-aminophenol | 1.5 g | | |
| 2-methyl-5-methylaminophenol | | | 0.8 g |
| 2-methyl-5-ethylamonophenol | | | 0.8 g |
| 2-methyl-5-N-(β-hydroxyethyl)-aminophenol | | 1.5 g | |
| 2-methoxymethyl-para-aminophenol | 0.5 g | 0.5 g | 1 g |
| pH of the mixture applied to the | 9.7 | 9.8 | 9.6 |
| SHADE OBTAINED: | | | |
| on natural grey hair containing 90% white hair | | Iridescent copper blond | Golden ash blond |
| on permanent-waved grey hair containing 90% white hair | | Dark golden copper blond | |

Dyeing at Acidic pH

EXAMPLE 4

The following dyeing composition is prepared:

| | |
|---|---|
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oxyethylenated oleic amine containing 2 mol of ethylene oxide, sold under the name ETHOMEEN O12 by the company AKZO | 7.0 g |
| Diethylaminopropyl laurylaminosuccinamate, sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% of AM | 0.46 g AM |
| Ammonium acetate | 0.8 g |
| Antioxidant, sequestering agent | qs |
| Perfume, preservative | qs |
| Monoethanolamine | 0.8 g |
| Colouring agents | x g |
| Demineralized water | qs 100 g |

The pH of the dyeing composition of Example 4 before mixing is 8.8.

At the time of use, the dyeing composition is mixed weight for weight with hydrogen peroxide titrating at 20 volumes (6% by weight) and the pH of which is adjusted to 1.4 by 1.7 g of orthophosphoric acid per 100 g of hydrogen peroxide.

A mixture is obtained the pH of which is indicated in the table below.

This mixture is applied to hair for 30 minutes. After rinsing, washing with shampoo, rinsing and drying, the hair is dryed in the shade indicated in the table below.

| Example | 4 |
|---|---|
| 3-methyl-p-aminophenol | 0.8 g |
| 2-methyl-p-aminophenol | 0.5 g |
| 2-ethoxymethyl-p-aminophenol hydrochloride | 0.5 g |
| 2-(β-hydroxyethoxy)methyl-p-aminophenol hydrochloride | 0.5 g |
| pH of the mixture | 7 |
| SHADE OBTAINED: on natural grey hair containing 90% white hair | Iridescent copper blond |

We claim:

1. A composition for dyeing keratinous fibers comprising in a medium suitable for dyeing said fibers,
    (a) at least one oxidation dye precursor selected from the group consisting of 2-methyl-para-aminophenol and an acid addition salt thereof;
    (b) at least one coupling agent comprising a 2-methyl-5-aminophenol of formula (I):

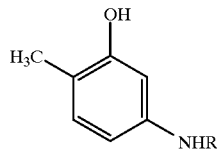

(I)

wherein
    R represents methyl, ethyl, or γ-hydroxypropyl or an acid addition salt thereof; and
    (c) at least one oxidation dye precursor comprising a 2-substituted para-aminophenol of formula (II):

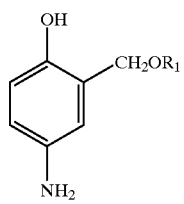

(II)

wherein
    $R_1$ represents $C_1$–$C_6$ arkyl, $C_1$–$C_6$ hydroxyalkyl, $C_2$–$C_6$ polyhydroxyalkyl, $C_1$–$C_6$ haloalkyl, $C_2$–$C_4$ aminoalkyl wherein the amino moiety is mono- or disubstituted with a $C_1$–$C_4$ alkyl or substituted with a $C_3$–$C_4$ dihydroxyalkyl, or an acid addition salt thereof.

2. A composition for dyeing keratinous fibers comprising in a medium suitable for dyeing said fibers,
    (a) at least one oxidation dye precursor selected from the group consisting of 3-methyl-para-aminophenol, 2-hydroxymethyl-para-aminophenol and an acid addition salt thereof;
    (b) at least one coupling agent comprising a 2-methyl-5-aminophenol of formula (I):

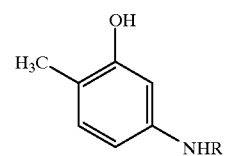

(I)

wherein
    R represents hydrogen, methyl, ethyl, β-hydroxyethyl or γ-hydroxypropyl or an acid addition salt thereof; and
    (c) at least one oxidation dye precursor comprising a 2-substituted para-aminophenol of formula (II):

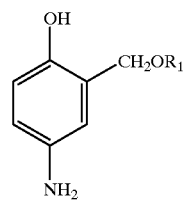

(II)

wherein
    $R_1$ represents $C_1$–$C_6$ alkyl, $C_1$–$C_6$ hydroxyalkyl, $C_2$–$C_6$ polyhydroxyalkyl, $C_1$–$C_6$ haloalkyl, $C_2$–$C_4$ aminoalkyl or $C_2$–$C_4$ aminoalkyl wherein the amino moiety is mono- or disubstituted with a $C_1$–$C_4$ alkyl or sjbstituted with a $C_3$–$C_4$ dihydroxyalkyl, or an acid addition salt thereof.

3. The composition of claim 2 wherein said oxidation dye precursor (a) is 3-methyl-para-aminophenol or an acid addition salt thereof.

4. The composition of claim 2 wherein said coupling agent is selected from the group consisting of 2-methyl-5-aminophenol, 2-methyl-5-N-(β-hydroxyethyl)-aminophenol, 2-methyl-5-methylaminophenol, 2-methyl-5-ethylaminophenol, and an acid addition salt thereof.

5. The composition of claim 1 wherein said coupling agent is selected from the group consisting of 2-methyl-5-methylaminophenol, 2-methyl-5-ethylaminophenol, and an acid addition salt thereof.

6. The composition according to claims 1 or 2, wherein said 2-substituted para-aminophenol of formula (II) is 2-methoxymethyl-para-aminophenol or an acid addition salt thereof.

7. The composition according to claims 1 or 2, wherein said acid addition salt is a hydrochloride, a sulphate, a hydrobromide or a tartrate.

8. The composition according to claim 1 or 2, wherein said oxidation dye precursor (a) is present in an amount ranging from 0.01 to 4 percent by weight based on the total weight of said composition.

9. The composition according to claims 1 or 2, wherein said oxidation dye precursor (a) is present in an amount ranging from 0.1 to 2 percent by weight based on the total weight of said composition.

10. The composition according to claims 1 or 2, wherein said coupling agent of formula (I) or an acid addition salt thereof is present in an amount ranging from 0.05 to 5 percent by weight based on the total weight of said composition.

11. The composition according to claims 1 or 2, wherein said coupling agent of formula (I) or an acid addition salt thereof is present in an amount ranging from 0.1 to 3.5 percent by weight based on the total weight of said composition.

12. The composition according to claims 1 or 2, wherein said 2-substituted para-aminophenol of formula (II) or an acid addition salt thereof is present in an amount ranging from 0.05 to 4 percent by weight based on the total weight of said composition.

13. The composition according to claims 1 or 2, wherein said 2-substituted para-aminophenol of formula (II) or an acid addition salt thereof is present in an amount ranging from 0.2 to 2 percent by weight based on the total weight of said composition.

14. The composition according to claims 1 or 2, wherein the combined total concentration of said oxidation dye precursors and said coupling agent ranges from 0.15 to 10 percent by weight based on the total weight of said composition.

15. The composition according to claims 1 or 2, wherein the combined total concentration of said oxidation dye precursors and said coupling agent ranges from 0.4 to 7 percent by weight based on the total weight of said composition.

16. The composition according to claims 1 or 2, wherein the pH ranges from 3 to 10.5.

17. The composition according to claims 1 or 2, containing another coupling agent selected from the group consisting of
   (i) a benzene compound having at least 2 hydroxyl substituents or at least 2 amino substituents in a meta position with respect to each other;
   (ii) a benzene compound bearing at least 1 amino substituent and at least 1 hydroxy substituent in a meta position with respect to each other and which is different from said 2-methyl-5-aminophenol of formula (I);

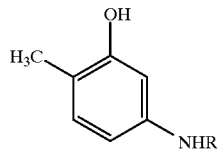

(iii) a-naphthol;
(iv) a pyrazolone; and a salt thereof.

18. The composition according to claims 1 or 2, additionally containing a direct dye selected from the group consisting of an azo dye, an anthraquinone dye and a nitrobenzene dye.

19. The composition according to claims 1 or 2, additionally containing at least one adjuvant selected from the group consisting of
   (i) an anionic, cationic, nonionic or an amphoteric surface-active agent or a mixture thereof, said surface-active agent being present in an amount ranging from 0.5 to 55 percent by weight based on the total weight of said composition;
   (ii) an organic solvent present in an amount ranging from 1 to 40 weight percent based on the total weight of said composition;
   (iii) a thickening agent present in an amount ranging from 0.1 to 5 weight percent based on the total weight of said composition; and
   (iv) an antioxidant present in an amount ranging from 0.05 to 1.5 weight percent based on the total weight of said composition.

20. The composition according to claims 1 or 2, also containing an additive selected from the group consisting of a penetration agent, a sequestering agent, a perfume, a buffer, a dispersing agent, a conditioning agent, a film-forming agent, a preservative and an opacifying agent.

21. A dyeing agent for keratinous fibers comprising a combination, in a medium suitable for dyeing said fibers, of
   (a) a component (A) comprising said composition according to claims 1 or 2; and
   (b) a component (B) comprising an oxidizing agent.

22. The dyeing agent of claim 3 wherein said oxidizing agent is selected from the group consisting of hydrogen peroxide, urea peroxide, an alkali metal bromate, a perborate and a persulphate.

23. A method of dyeing keratinous fibers comprising
   (a) applying to said fibers in an amount effective to dye said fibers said composition according to claims 1 or 2, and
   (b) developing a coloration on said fibers by applying to said fibers an acidic so alkaline medium containing an oxidizing agent added to said composition at the moment of applying said composition to said fibers or applying to said fibers, simultaneously or in a separate manner, a composition comprising an oxidizing agent.

24. The method of claim 23 comprising admixing said composition of step (a) at the time of application to said fibers with an oxidizing agent in an amount sufficient to develop a coloration on said fibers, applying the resulting mixture to said fibers and permitting it to remain thereon for a period of time ranging from 5 to 40 minutes and thereafter rinsing, washing with shampoo, again rinsing and drying said fibers.

25. A multi-compartment kit for dyeing keratinous fibers comprising a first compartment containing a composition (A) comprising the keratinous fiber dyeing composition according to claims 1 or 2, and a second compartment containing a composition (B) comprising an oxidizing agent present in a medium suitable for dyeing said fibers.

26. The composition according to claim 1 wherein $R_1$ of formula (II) is $C_1$–$C_6$ alkyl or an acid addition salt thereof.

* * * * *